US011046623B1

(12) United States Patent
Dagle et al.

(10) Patent No.: US 11,046,623 B1
(45) Date of Patent: Jun. 29, 2021

(54) CATALYTIC CONVERSION OF ETHANOL TO 1-/2-BUTENES

(71) Applicant: BATTELLE MEMORIAL INSTITUTE, Richland, WA (US)

(72) Inventors: Vanessa M. Dagle, Richland, WA (US); Robert A. Dagle, Richland, WA (US)

(73) Assignee: BATTELLE MEMORIAL INSTITUTE, Richland, WA (US)

(*) Notice: Subject to any disclaimer, the term of this patent is extended or adjusted under 35 U.S.C. 154(b) by 0 days.

(21) Appl. No.: 16/871,285

(22) Filed: May 11, 2020

Related U.S. Application Data

(63) Continuation-in-part of application No. 15/994,531, filed on May 31, 2018, now Pat. No. 10,647,622.

(60) Provisional application No. 62/944,749, filed on Dec. 6, 2019.

(51) Int. Cl.
C07C 1/20 (2006.01)
C07C 11/08 (2006.01)

(52) U.S. Cl.
CPC .............. *C07C 1/20* (2013.01); *C07C 11/08* (2013.01); *C07C 2521/06* (2013.01); *C07C 2523/50* (2013.01); *C07C 2529/035* (2013.01)

(58) Field of Classification Search
CPC ........... C07C 1/20; C07C 1/24; C07C 1/2078; C07C 2523/06
See application file for complete search history.

(56) References Cited

U.S. PATENT DOCUMENTS

| | | | | |
|---|---|---|---|---|
| 10,647,622 | B1* | 5/2020 | Dagle | B01J 29/043 |
| 2016/0082417 | A1* | 3/2016 | Lewandowski | B01J 23/10 |
| | | | | 585/607 |
| 2017/0267604 | A1* | 9/2017 | Dastillung | B01D 3/14 |
| 2018/0208522 | A1* | 7/2018 | Cadran | B01J 37/08 |

OTHER PUBLICATIONS

Sushkevich et al. ("Design of a Metal-Promoted Oxide Catalyst for the Selective Synthesis of Butadiene from Ethanol", ChemSusChem 2014, 7, 2527-2536) (Year: 2014).*
Sun et al. ("Catalysis Chemistry of Dimethyl Ether Synthesis", ACS Catal. 2014, 4, 3346-3356) (Year: 2014).*
Jones et al. ("Investigations into the conversion of ethanol into 1,3-butadiene", Catal. Sci. Technol., 2011, 1, 267-272 and Supporting Information) (Year: 2011).*

* cited by examiner

Primary Examiner — Youngsul Jeong
(74) Attorney, Agent, or Firm — Derek H. Maughan

(57) ABSTRACT

Simple and economical conversion of aqueous ethanol feed streams into butenes by a single step method using transition metal oxides on a silica supports under preselected processing conditions. By directly producing a C4-rich olefin mixture from an ethanol containing stream various advantages are presented including, but not limited to, significant cost reduction in capital expenses and operational expenses.

3 Claims, 6 Drawing Sheets

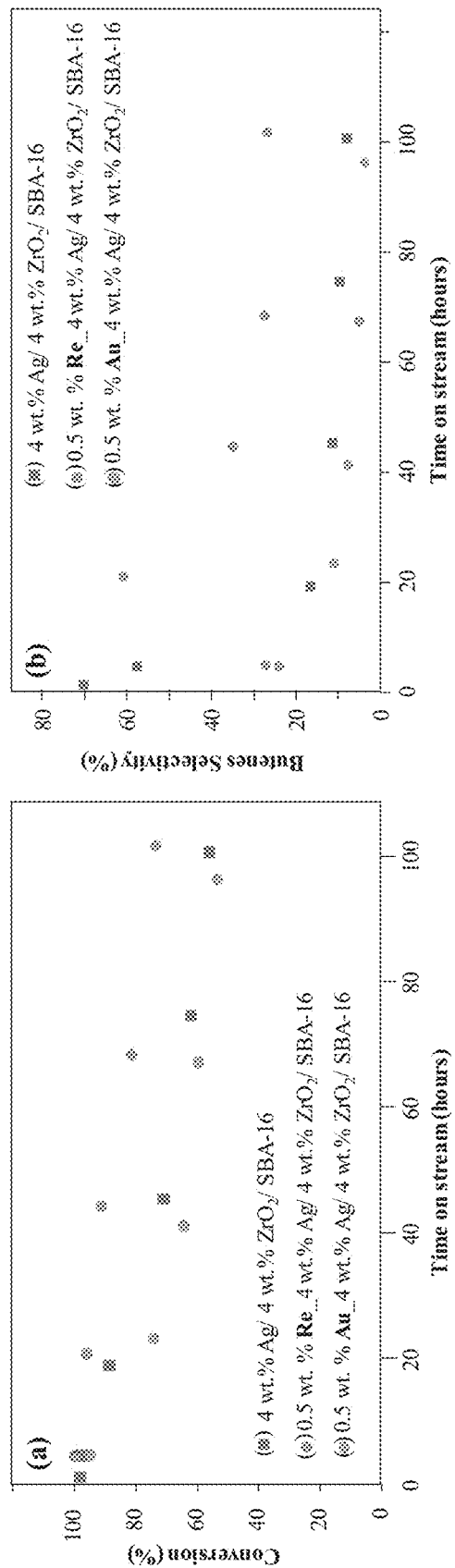

CATALYTIC CONVERSION OF ETHANOL TO 1-/2-BUTENES

CLAIM TO PRIORITY

This application claims priority from and is a continuation in part of U.S. patent application Ser. No. 15/994,531 filed by the same inventors on May 31, 2018, as well as provisional application No. 62/944,749 filed on Dec. 6, 2019. The contents of both of these references are incorporated herein in their entirety.

STATEMENT AS TO RIGHTS TO DISCLOSURES MADE UNDER FEDERALLY-SPONSORED RESEARCH AND DEVELOPMENT

This disclosure was made with Government support under Contract DE-AC0576RL01830 awarded by the U.S. Department of Energy. The Government has certain rights in the invention.

BACKGROUND OF THE DISCLOSURE

Petroleum depletion and environmental issues caused by the chemical and petrochemical industries have led to a renewal of interest for using biomass as a carbon source for biofuels production. Various research organizations including program offices within the United States Department of Energy have sought, and continue to seek, transformative and revolutionary sustainable bioenergy technologies. Ethanol conversion to biofuels is one of these attractive bioenergy technologies. Ethanol can be commercially produced at large scale from renewable biomass or waste sources, and continuing advancements in production efficiency and feedstock diversification are envisioned to lead to excess ethanol at competitive prices. The broad availability and cost effective supply of ethanol as a feed stock would enable the production of a wide range of fuels and commodity chemicals.

While ethanol supplies are predicted to rise, a reduction in supplies of other commodity chemicals is also expected. A variety of approaches have been taken attempting to identify simple and cost effective processes for generating desired fuels and commodity chemicals in newer, greener and more cost efficient ways. While a variety of processes have been shown to have some efficacy continued development is needed to find methods that can simply and cost effectively produce the desired result and do so in a sufficiently cost effective manner so as to be adopted in industrial and commercial applications. The present disclosure describes significant advances in this regard.

Additional advantages and novel features of the present disclosure will be set forth as follows and will be readily apparent from the descriptions and demonstrations set forth herein. Accordingly, the following descriptions of the present disclosure should be seen as illustrative of the disclosure and not as limiting in any way.

SUMMARY

The following description provides examples and information surrounding simple and economical conversion of (aqueous) ethanol into butenes, such as 1-butene. As will be explained below in further detail, oligomerization of mixed 1- and 2-butenes, produced by the single step methods described hereafter allow for the creation of various hydrocarbon fuel configurations both in the presence of and/or absence of hydrogen and/or ethylene. By directly producing a C4-rich olefin mixture (that can then be selectively oligomerized into gasoline, jet and/or diesel fuels) from an ethanol containing stream various advantages are presented including, but not limited to, significant cost reduction in capital expenses and operational expenses as this simplified process allows for a closer term transformation of a feedstock to a useable product without many of the preprocessing and water/ethanol separations steps that other processes require.

As the data provided in the detailed description demonstrates, transition metal oxide catalysts on a silica support with higher % of transition metal dispersion provide Lewis acid sites in a desired range which provide desired conversion and selectivity toward the creation of desired butenes. butadiene partial hydrogenation in the presence of H2 carrier and butadiene is produced from acetaldehyde over the acid sites. These structures and process take advantage of the relatively weak hydrogenation ability of the transition metals and mildly acidic support materials provide a preference for carbon to oxygen and carbon to carbon coupling take place without hydrogen saturation.

This direct conversion of ethanol to butenes can be conducted one single reactor while it is not always necessary do so. The present process was also demonstrated using an aqueous ethanol feedstock indicating that typical ethanol/water separations required by many prior art processes is not always be necessary. This coupled with a reduction of stages in additional chemical processing and allows for various simplified operation units, which can present a significant step forward in reducing costs and complexities and moving production of renewable transportation fuels forward toward a practical reality.

In one set of embodiments, the process for producing butene from a feed stream containing ethanol in a single step is described wherein a feed containing ethanol in a gas phase is passed over a catalyst having a transition metal oxide with a transition metal dispersion of at least 30% on a silica support. A hydrogen containing carrier gas assists in the feed flow and a preselected temperatures and preselected pressures butenes form from the ethanol with selectivity equal or greater than 13%. In one instance, the transition metal catalyst is a 4 weight % Ag/4 weight % $ZrO_2$/$SiO_2$-SBA-16 catalyst, in other instances the transition metal catalyst is a 4 wt. % Cu/4 wt. % $ZrO_2$/SBA-16 catalyst. In others a 0.5 wt. % Au_4 wt. % Ag/4 wt. % $ZrO_2$/SBA-16, while in others the catalyst is 0.5 wt. % Re_4 wt. % Ag/4 wt. % $ZrO_2$/SBA-16. A 1% Ag/4% $ZrO_2$/$SiO_2$-SBA-16 has also been successfully utilized.

While these examples are provided, they are not intended to a limiting or comprehensive list but instead are intended to demonstrate examples of the catalyst materials that practice of the invention described in the claims can utilize. The process of claim 1 wherein the silica support is a high purity SBA16.

In one embodiment the ethanol feed is provided at a pressure of 1 atm, and a flow rate of 0.23 hr-1. A variety of variations can also be utilized, typically the ethanol feed is a mixture containing at least 10 percent ethanol and includes water. However, variation and alteration are also possible according to the needs of a user. In practice temperatures between 200 degrees C. and 500 degrees C. have demonstrated efficacy with specific experiments run at 325 degrees C., and 400 degrees C. provided. Similarly, pressures between 1 atm and 100 atm have been run with specific examples at 1 atm, 7 atm and 70 atm. While specific examples of experiments demonstrating the efficacy of invention have been provided and described these examples are merely illustrative and not limited to the examples provided therein.

The purpose of the foregoing abstract is to enable the United States Patent and Trademark Office and the public generally, especially the scientists, engineers, and practitioners in the art who are not familiar with patent or legal terms or phraseology, to determine quickly from a cursory inspection the nature and essence of the technical disclosure of the application. The abstract is neither intended to define the disclosure of the application, which is measured by the claims, nor is it intended to be limiting as to the scope of the disclosure in any way.

BRIEF DESCRIPTION OF THE DRAWINGS

FIG. 6(a) shows the conversion with time on stream for 4 wt. % Ag/4 wt. % ZrO$_2$/SBA-16 catalyst and 0.5 wt. % Au_4 wt. % Ag/4 wt. % ZrO$_2$/SBA-16 at T=400° C., P=7 bar, WHSV=1.82 hr$^{-1}$, 24% ethanol in H$_2$.

FIG. 6(b) shows the butenes selectivity with time on stream for 4 wt. % Ag/4 wt. % ZrO$_2$/SBA-16 catalyst and 0.5 wt. % Au_4 wt. % Ag/4 wt. % ZrO$_2$/SBA-16 at T=400° C., P=7 bar, WHSV=1.82 hr$^{-1}$, 24% ethanol in H$_2$.

DETAILED DESCRIPTION OF THE DISCLOSURE

The following description includes examples of exemplary modes of implementation. It will be clear from this description of the disclosure that the invention is not limited to these illustrated embodiments but that the disclosure also includes a variety of modifications and embodiments thereto. Therefore, the present description should be seen as illustrative and not limiting. While the disclosure is susceptible of various modifications and alternative constructions, it should be understood, that there is no intention to limit the disclosure to the specific form disclosed, but, on the contrary, the disclosure is to cover all modifications, alternative constructions, and equivalents falling within the spirit and scope of the disclosure as defined in the claims.

The present disclosure includes a series of examples for methods and materials for converting ethanol in a gas feed (including a water containing or steam ethanol feed) into a preselected commodity chemical such as butene. In one embodiment, this is performed by the single step conversion of ethanol (either aqueous or neat) to 1- and 2-butenes, which can be oligomerized into a variety of materials including gasoline, jet, and diesel fuels and/or into valuable fuel additives and lubricants. This provides a significant advantage over the prior art inasmuch as production of 1- and 2-butene from ethanol is typically performed by first dehydrating ethanol into ethylene and then dimerizing ethylene into 1- and 2-butene in a second step. However as described hereafter, methods for producing 1- and 2-butene mixtures directly from ethanol (in some cases included in a water and ethanol mixture) have been developed that remove this step and make the use of ethanol as a fuel base more practical and economical.

The process uses specially tailored polyfunctional catalysts having a metal component with relatively weak hydrogenation ability (e.g., Ag) and mildly acidic support materials (e.g., ZrO$_2$ supported on SiO$_2$). These catalysts allow for carbon to oxygen and carbon to carbon coupling without saturation of the material with hydrogen. This is believed to be obtained by taking advantage of the various oxidation states of a metal (such as silver) and the Lewis Acid site (i.e., acidity) nature of the catalysts. Under certain process conditions, as shown in the attached tables and figures, direct formation of butenes from an ethanol stream in a gaseous phase, without the need for additional process steps as required by the prior art embodiments.

Figure 1:
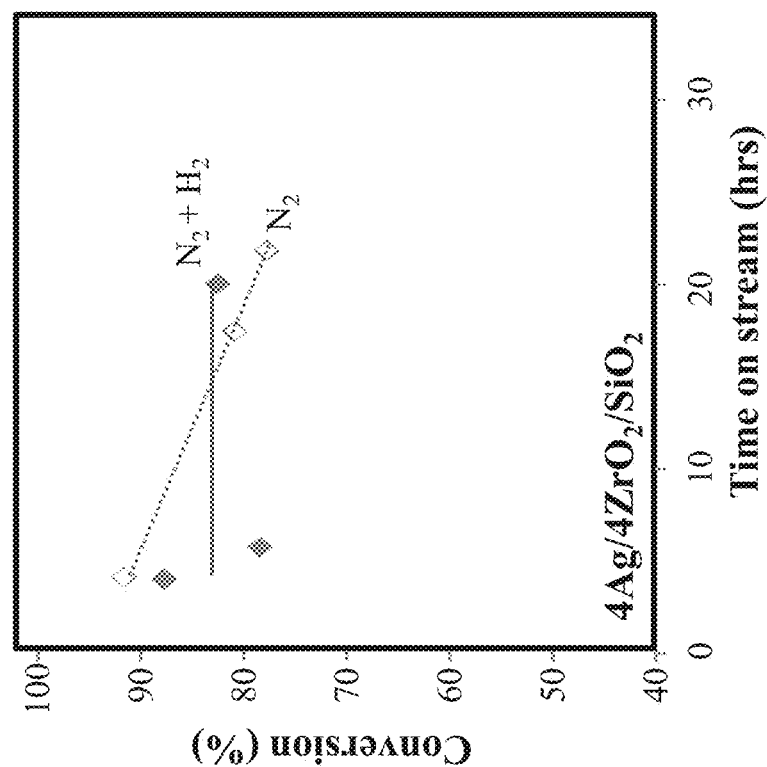
FIG. 1 shows ethanol conversion as a function of time in a first embodiment of the invention.
Figure 2:
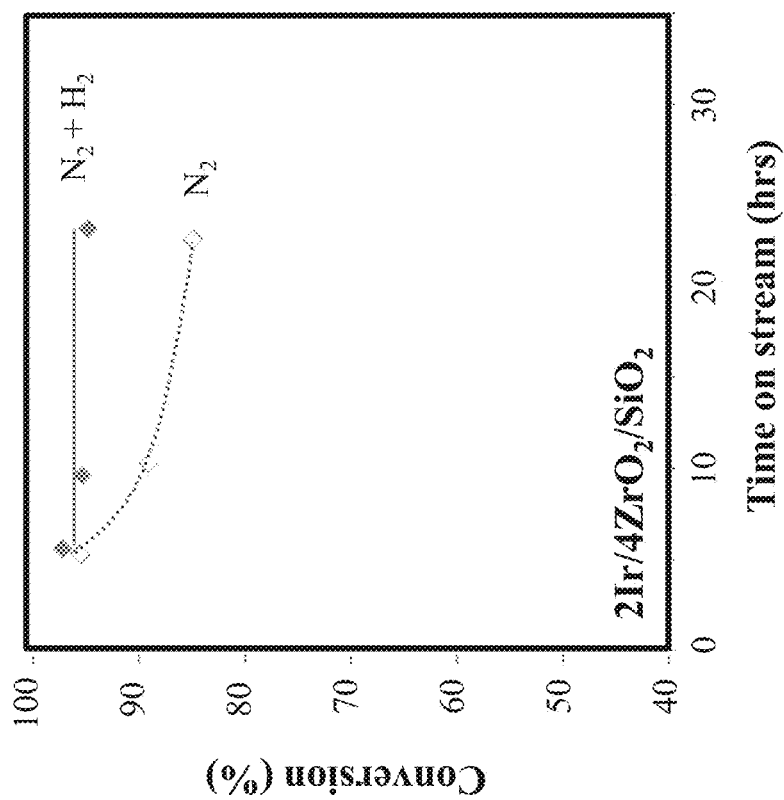
FIG. 2 shows ethanol conversion as a function of time in a second embodiment of the invention.

A first set of examples are shown in FIGS. 1 and 2 wherein the time on stream in hours and the conversion percentages are shown for particular embodiments. In one example a 24.3% ethanol feed in a N2 or N2 and H2 mixture is shown passing over a 2Ir/4ZrO$_2$/SiO$_2$ catalyst (FIG. 1) or a 4Ag/4ZrO$_2$/SiO$_2$ (DAVISIL 646) catalyst (FIG. 2) under the following conditions. Temperature 325 degrees C., Pressure 1 atm, WHSV 0.23/hr. As these figures show conversion percentages are relatively high (>75 percent) over a designated period of time. While these exemplary samples are provided it is to be distinctly understood that the invention are not limited to these examples but may be variously alternatively embodied as necessary.

In another example a 24% ethanol feed in a gaseous state was passed over a 4Ag/4ZrO$_2$/SiO$_2$/SBA16 catalyst under the following conditions: temperature 325° C., pressure=7 bar (100 psig), flow rate (space velocity) WHSV=0.23 hr-1. An incremental addition of H$_2$ to the feed gas from 0% to 100% (carrier gas content) was varied and produced the results shown in Table 1.

TABLE 1

| | H2% | | | |
|---|---|---|---|---|
| | 0% H2 | 18.5% H2 | 45% H2 | 100% H2 |
| Carbon Balance | 91.0 | 89.0 | 96.3 | 97.5 |
| Conversion % | 99 | 98 | 95.9 | 85.2 |
| C2= | 8.6 | 6.2 | 9.6 | 25.8 |
| C3= | 0.0 | 2.0 | 2.5 | 3.2 |
| C4= | 15.8 | 35.3 | 41.7 | 51.1 |
| C5= | 0.9 | 1.8 | 1.5 | 0.7 |
| BD Butadiene | 63.7 | 6.6 | 1.2 | 0.4 |
| C2-C6 alkanes | 0.5 | 1.3 | 2.0 | 2.8 |

TABLE 1-continued

| | H2% | | | |
|---|---|---|---|---|
| | 0% H2 | 18.5% H2 | 45% H2 | 100% H2 |
| Acetaldehyde HAC | 2.9 | 0.7 | 0.8 | 2.3 |
| Other Oxygenates (e.g. C1-C4 alcohols, Ethyl acetate, acetic acid, 2-butanone, acetone) | 3.8 | 7.5 | 10.2 | 5.3 |
| Crotonaldehyde | 0.7 | 0 | 0 | 0 |
| Diethylether | 3.1 | 4.1 | 4.0 | 8.4 |
| C4-C8 olefins Liquid | 0 | 10.0 | 11.9 | 0 |
| Cyclic Hydrocarbon Liquids | 0 | 24.5 | 14.6 | 0 |
| Olefins w/o Butadiene Total Gas and Liquid | 25.3 | 55.3 | 67.2 | 80.8 |
| Olefins w/o Butadiene Total in gas | 25.3 | 45.3 | 55.3 | 80.8 |

As the data in this table shows, as the percentage of hydrogen increases the percentage of the ethanol converted decreases from 99 to 85% accompanied by an increase of the 1- and 2-butene combined selectivity from ~16 to 51%. Meanwhile the ethylene selectivity increased from ~8.6 to 26% while the butadiene selectivity decreased from 63.7% to 0%. Generally speaking, 1- and 2-butene is formed at the expense of 1,3-butadiene when $H_2$ content is added to the feed. Table 2 shows the effect of altering the flow rate (space velocity) on catalytic performance for the conversion of ethanol to butenes over this same catalytic composition.

TABLE 2

Effect of flow rate (space velocity) variation on catalytic performance

| Run ID | | 227 | 243 | 272 | 237 | 253 | 231 | 233 | 235 |
|---|---|---|---|---|---|---|---|---|---|
| Pressure (Psig) | | 100 | 100 | 100 | 100 | 100 | 100 | 100 | 100 |
| WHSV (hr−1) | | 0.10 | 0.23 | 0.7 | 1.4 | 2.0 | 3.6 | 7.3 | 14.6 |
| Conversion (%) | | 87.6 | 87.1 | 75.3 | 67.5 | 65.7 | 65.5 | 34.9 | 11.7 |
| Carbon Balance | | 85 | 104 | 104 | 112 | 95.5 | 91 | 103 | 104 |
| Selectivity % | butadiene | 0.0 | 3.8 | 4.2 | 19.5 | 0.6 | 0 | 0 | 0 |
| | C2= | 7.1 | 16.7 | 2.9 | 13.1 | 10.6 | 9.0 | 11.1 | 15.0 |
| | C3= | 1.0 | 2.7 | 1.2 | 1.5 | 1.7 | 1.2 | 0.9 | 0.8 |
| | C4= | 47.3 | 40.7 | 46.3 | 24.3 | 51.1 | 51.9 | 27.9 | 13.0 |
| | C5= | 0.2 | 0.6 | 1.0 | 0.3 | 0.2 | 0.5 | 0.3 | 0.0 |
| | Diethylether | 10.2 | 8.6 | 3.3 | 6.8 | 6.2 | 6.5 | 6.5 | 7.7 |
| | Acetaldehyde | 0.6 | 1.4 | 3.1 | 3.7 | 7.2 | 8.1 | 18.6 | 26.5 |
| | C2-C5 Alkanes | 14.6 | 1.6 | 0.8 | 1.0 | 2.5 | 1.7 | 1.0 | 0.9 |
| | C4+ Alkanes Liquids | 6.9 | 0 | 0 | 0 | 0 | 0 | 0 | 0 |
| | Butyraldeheyde | 0 | 1.9 | 2.1 | 15.5 | 16.2 | 17 | 26.1 | 31.4 |
| | C4-C8 olefins liquids | 4.2 | 11.0 | 16.1 | 0 | 0 | 0 | 0 | 0 |
| | butanol | 0 | 0.1 | 1.2 | 0.2 | 1.7 | 1.7 | 1.8 | 1.2 |
| | Others (e g. cyclic hydrocarbons and oxygenates (e.g. C1-C4 alcohols, ethyl acetate, acetic acid, 2-butanone, acetone) | 15.0 | 10.9 | 17.8 | 14.1 | 2.0 | 2.4 | 6.8 | 3.5 |
| | Total olefins | 59.8 | 71.7 | 67.5 | 39.2 | 63.6 | 62.6 | 40.2 | 28.8 |

Table 3 shows the effect of pressure on catalytic performance for the conversion of ethanol to butenes on a 4Ag/4ZrO$_2$/SiO$_2$/SBA16 catalyst under the following conditions: temperature 325° C., pressure=7 bar (100 psig), 24% ethanol in hydrogen gas, time on stream (TOS) 5 hours.

TABLE 3

| Run ID | | MO236 | MO237 | MO216 |
|---|---|---|---|---|
| Pressure (Psig) | | Atm | 100 | 200 |
| WHSV (hr−1) | | 1.4 | 1.4 | 1.4 |
| Conversion % | | 53.4 | 67.5 | 82.5 |
| Carbon Balance | | 110 | 112 | 106 |
| Selectivity % | butadiene | 43.8 | 19.5 | 0 |
| | C2= | 22.2 | 13.1 | 7.1 |
| | C3= | 1.2 | 1.5 | 0 |
| | C4= | 8.2 | 24.3 | 28.2 |
| | diethylether | 11.3 | 6.8 | 8.2 |
| | acetaldehyde | 8.1 | 3.7 | 2.7 |
| | butyraldehyde | 2.1 | 15.5 | 3.8 |
| | BuOH | 0.6 | 0.2 | 2.3 |
| | C2-C5 alkanes | 0.2 | 1.0 | 9.0 |
| | C4-C8 olefins in liquid | 0 | 0 | 16.0 |
| | Others (e.g. cyclic hydrocarbons and oxygenates (C1-C4 alcohols, ethyl acetate, acetic acid, 2-butanone, acetone) | 2.3 | 14.4 | 20.6 |
| | C6-C7 alkanes | 0 | 0 | 2.1 |
| | Total olefins | 31.6 | 38.9 | 51.3 |

Table 4 shows the effect of water content in the ethanol feed stream on the conversion of ethanol to butenes on a 4Ag/4ZrO$_2$/SiO$_2$/SBA16 catalyst under the following conditions: temperature 325° C., pressure=7 bar (100 psig), 11% ethanol in gas, flow rate (space velocity) WHSV=0.23 hr$^{-1}$.

TABLE 4

| | Feed Composition | | |
|---|---|---|---|
| | Pure EtOH | 95% EtOH in H2O | 35% EtOH in H2O |
| Pressure (Psig) | 100 | 100 | 100 |
| WHSV (hr-1) | 0.23 | 0.23 | 0.23 |
| Conversion % | 93.9 | 93.9 | 76.4 |
| Carbon Balance | 120 | 112 | 103 |
| Selectivity % butadiene | 0 | 0 | 0 |
| C2= | 25.7 | 19.4 | 8.8 |
| C3= | 2.0 | 1.6 | 2.1 |
| C4= | 57.7 | 56.9 | 54.8 |
| diethylether | 6.0 | 6.1 | 2.8 |
| acetaldehyde | 0.4 | 0.3 | 6.5 |
| butyraldehyde | 0.1 | 0.1 | 2.3 |
| BuOH | 0 | 0 | 2.6 |
| C2-C5 alkanes | 6.1 | 12.9 | 2.1 |
| C4-C8 olefins in liquid | 0 | 0 | 0 |
| Acetic Acid | 0.7 | 0.5 | 11.8 |
| Others (cyclic hydrocarbons and oxygenates (C1-C4 alcohols, ethyl acetate, acetic acid, 2-butanone, acetone) | 1.3 | 2.2 | 6.2 |
| Total olefins | 85.4 | 77.9 | 65.7 |

In addition to these results we also demonstrated that catalytic stability is enhanced when $H_2$ is added to $N_2$ as the carrier gas for the process. (See FIGS. 1 and 2) Hence the addition of $H_2$ (to the ethanol feed) not only alters the product distribution favoring a butene product slate but it also significantly suppresses coking allowing for enhanced catalytic stability. While $H_2$ addition to the feed may add cost to the overall process, hydrogen is usually needed anyhow for fuels production as the final olefin product after oligomerization needs to be hydrotreated. Thus, the added hydrogen can be used in the latter hydrotreatment step and unconverted hydrogen can be recycled to the front end of the process.

Higher contact times favor the formation of 1- and 2-butenes. Decreasing the space velocity from 14.6 to 0.23 hr-1 while operating under $H_2$ gas leads to an increase of the conversion from ~11 to 85% and an increase of both 1- and 2-butenes and ethylene selectivity from ~13 to 51% and ~15 to 26%, respectively. In addition the fractions transition to acetaldehyde and butyraldehyde decrease while the effect on butadiene selectivity remains negligible. This suggests that the mechanism for butene formation involves the conversion of acetaldehyde to crotyl alcohol, isomerization of crotyl alcohol to butyraldehyde, and butenes formation from butyraldehyde deoxygenation. The effect of operating pressure was also investigated. In this review it was found that higher pressure favors the formation of butenes at the expense of butadiene (see Table 3).

For example, increasing the pressure from atmospheric to 14 bar while operating under $H_2$ gas leads to an increase of the conversion from 52 to 83% and an increase of the C4+ olefins selectivity from 8.1 to 44% while the selectivity toward butadiene and ethylene decreases from 43 to 0% and 22 to 7%, respectively. Addition of water to the feed also leads to a decrease of the conversion, from 94.0%, with 100% ethanol as a feedstock, and to 76%, with 35% ethanol in $H_2O$ as a feedstock (see Table 4). The butenes selectivity is only slightly affected by the presence of water since it decreases from 58% to 55%. However, this demonstrates that diluted feeds of ethanol can be used as feedstock and separation of water and ethanol is not required prior to conversion. In addition alteration and modification of a variety of other factors including $H_2$ concentration, $H_2O$ concentration, space velocity and pressure were demonstrated to have significant effect on conversion, selectivity, and stability. $H_2$-addition to the feed favors the formation of 1- and 2-butene at the expense of butadiene.

The product from the ethanol conversion contains primarily butenes and ethylene olefins mixed with $H_2$ which can be oligomerized for the formation of fuels. In a series of experiments intended to demonstrate the feasibility of producing fuels from the olefin precursors obtained from the single step process we co-feed ethylene and/or $H_2$ with butene mixtures over zeolite catalysts and obtained favorable results. Table 5 shows the results of this testing under the following conditions. Zeolite beta catalyst, temperature 260 degrees C.; pressure 200 psig; WHSV 0.42-46 hr-1. Time on stream extended up to 50 hours.

TABLE 5

| | Olefin Liquid Products (mg/min/gram catalyst) | | | | | | | | | | | |
|---|---|---|---|---|---|---|---|---|---|---|---|---|
| Feed | C4 | C5 | C6 | C7 | C8 | C9 | C10 | C11 | C12 | C13 | C14 | C15 |
| 1-butene | 2.2 | 0.0 | 0.6 | 8.7 | 50.0 | 10.3 | 3.3 | 4.0 | 43.4 | 3.9 | 0.7 | 5.2 |
| H2 + 1-butene | 3.0 | 0.4 | 2.3 | 6.6 | 36.2 | 12.9 | 8.7 | 7.6 | 28.0 | 2.4 | 1.5 | 0.5 |
| C2= + 1-butene | 3.8 | 1.3 | 4.1 | 11.2 | 55.8 | 16.5 | 9.0 | 10.3 | 37.2 | 4.6 | 4.2 | 0.0 |
| H2 + C2= + 1 butene | 3.8 | 1.4 | 4.6 | 12. | 53.9 | 14.1 | 7.8 | 15.2 | 38.5 | 4.7 | 1.8 | 0.0 |

These results show that oligomerization of butenes in the presence of H2 was feasible. Adding $H_2$ to the feed leads to about 20% lower C8+olefins production. Adding ethylene to the feed was also demonstrated to lead to higher paraffins/olefins ratio due to hydrogenation activity but does not affect the production of C8+olefins since the same quantity of product was obtained w and w/o ethylene addition to the feed. The ratio paraffins/olefins is equal to about 0.4 in the presence of H2+ethylene as opposed to <0.5 without $H_2$+ethylene indicating a significant hydrogenation activity. The quantity of C8 olefins produced is about 10% higher in the presence of H2 and ethylene and is likely due to ethylene oligomerization to C8+product occurring in the meantime as butenes oligomerization. Thus, we demonstrate that oligomerization of 1-butene is feasible in the presence of $H_2$ and/or ethylene co-feed.

The product distribution for 2-butene oligomerization to be very similar to that of 1-butene. Thus, a feed containing mixtures and 1- and 2-butene arising from the single step process would produce a similar product distribution when passed through this oligomerization step. This process provides a promising way for developing a bio-derived jet/diesel fuel from ethanol upon oligomerization followed by hydrogenation as demonstrated by this disclosure.

In another set of experiments various catalyst configurations were tested to determine the effect of various catalyst compositions and performance parameters on obtaining the desired outcomes. The following Table 6 presents the data from this testing. This data demonstrates that monitoring the quantity and quality of metals in the catalyst composition is important in maintaining desired performance. Experimental results have shown that when Ag percentages rise above 16 percent that saturation of the hydrocarbon increases and increased yields of C2-C5 alkanes begin to take place. We believe that this is due to the ability of Ag to become partially oxidized which may be a factor in hydrogenation suppression. Similarly, adding other metals with stronger hydrogenation capability such as Ir, Pd, or Pt will render a significant number of paraffins. These metals that are stronger for hydrogenation will also push toward the formation of alkanes rather than the desired alkenes. This was demonstrated even 0.4% Ir was added to the 4Ag/4Zr/SiO$_2$ system.

The temperature of the ethanol to butenes-rich olefins reaction was thus progressively increased while monitoring the ethylene and DEE formation.

Figure 3:
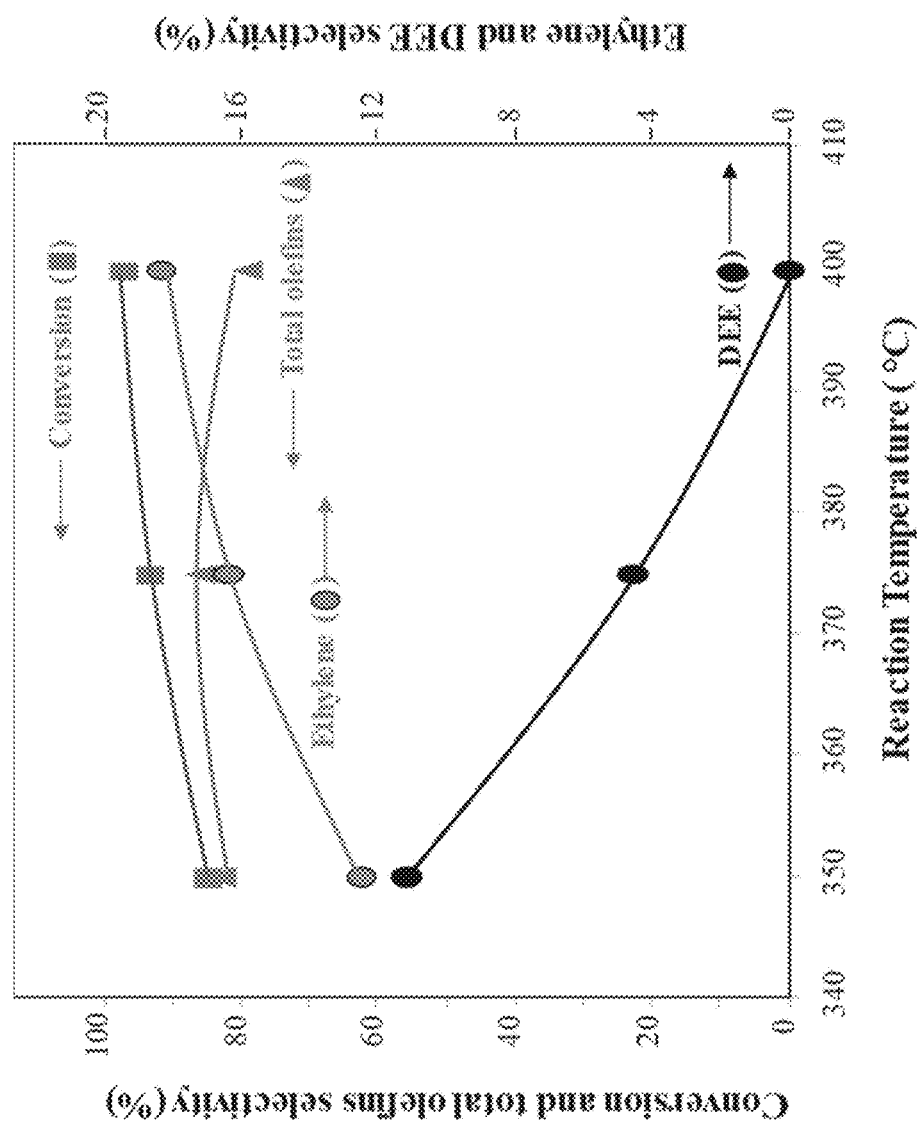
FIG. 3 is chart showing the effect of the reaction temperature on the conversion and selectivity for 4Ag/4ZrO$_2$/SBA-16. WHSV=0.91 hr$^{-1}$, P=7 bars, T=350-400° C., 24% ethanol in H$_2$.
Figure 4:
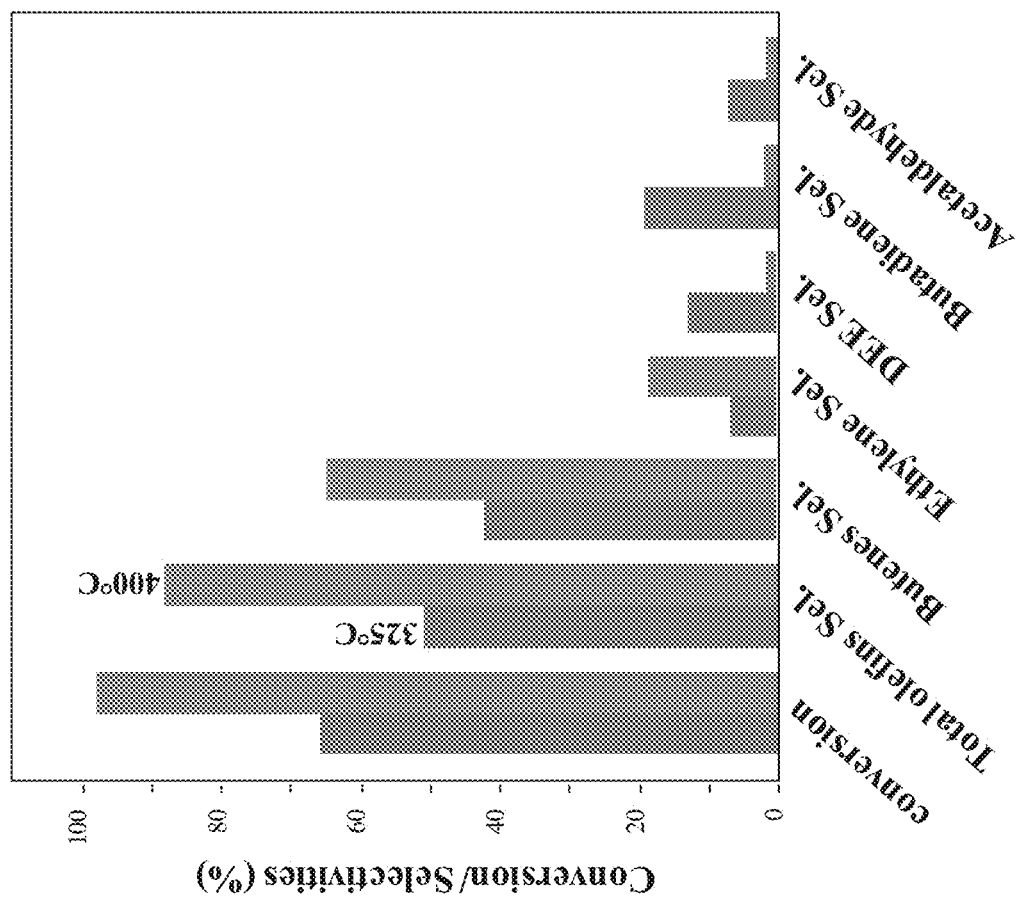
FIG. 4 is a chart showing the effects of the reaction temperature on the conversion and selectivity for 4Ag/4ZrO$_2$/SBA-16, P=7 bar, WHSV=1.4-1.8 hr$^{-1}$, 24% ethanol in H$_2$. T=325° C. left bars and T=400° C. right bars.

As shown in FIG. 3, DEE formation decreases with the increase of the temperature to the advantage of the ethylene formation. At 400° C., no DEE was detected under the present conditions. FIG. 4 presents the conversion and products selectivity obtained with 4Ag/4ZrO$_2$/SBA-16 while operating at 325° C. (baseline reaction temperature) and 400° C. The total desired olefins selectivity is equal to 88% at 400° C. and is 73% higher than that at 325° C. This is attributed to the increased ethylene/DEE ratio and the increased butadiene hydrogenation to butenes. Hence, an optimal butenes-rich olefins selectivity of 88% was obtained at 99% conversion while operating under H$_2$ at 7 bars of pressure and a reaction temperature of 400° C.

Figure 5B:
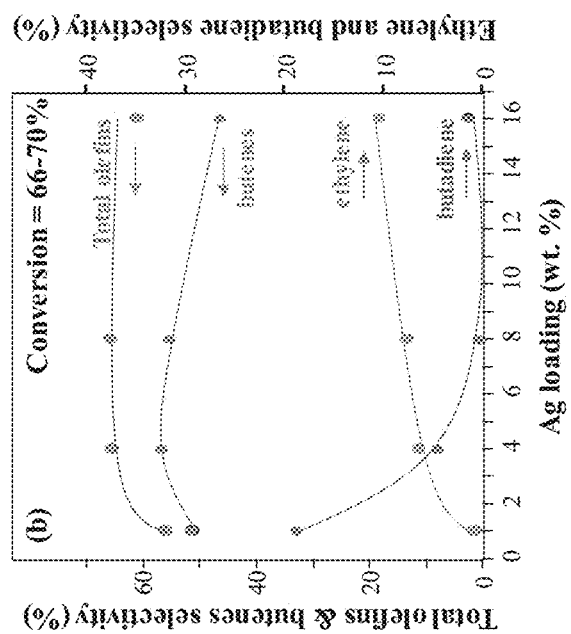
FIG. 5(b) shows the selectivity to butadiene, butenes and total olefins at 66-70% conversion. 4Ag/4ZrO$_2$/SBA-16 catalysts, T=325° C., P=7 bar, 24% ethanol in H$_2$.
Figure 5A:
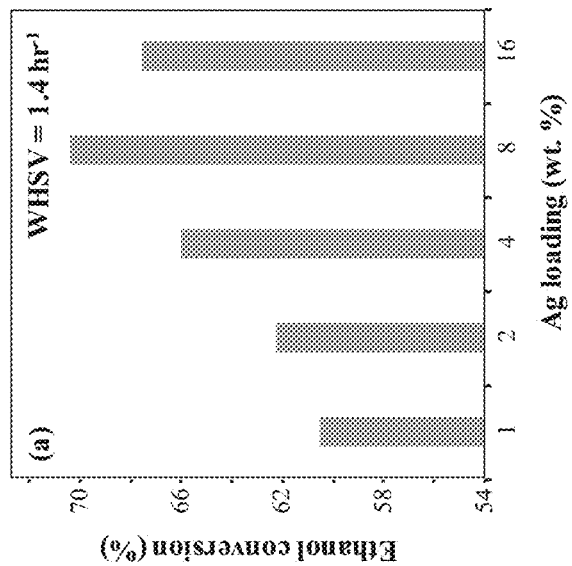
FIG. 5(a) shows the effect of the Ag loading on the ethanol conversion at WHSV=1.4 hr$^{-1}$.

A series of Ag/4ZrO$_2$/SBA-16 catalysts with Ag loading varying from 1 to 16 wt. % was tested for ethanol conversion in the presence of H$_2$ and the results are displayed in FIGS. 5(*a*) and 5(*b*). While the conversion increases from 60% to 70% with the increase of the Ag loading from 1 to 8 wt. %, a slight loss of conversion is observed at 16% loading. For Ag>8 wt %, increasing the Ag loading most likely leads to an increase of the Ag particles size rather than an increase of the concentration of active Ag sites resulting in a decrease of conversion. At similar conversion of 66-70%, the products

TABLE 6

Operating Conditions
Pressure 1000 psig, Temp 325 C., 24% EtOH in H2

| Catalyst | WHSV (hr-1) | Conv (%) | C bal | Selectivity (%) | | | | | | | | | | | | |
|---|---|---|---|---|---|---|---|---|---|---|---|---|---|---|---|---|
| | | | | B | C2= | C3= | C4= | C5= | D | A | C2-C5 Alkanes | BA | BL | MEK | Others* | Total olefins |
| 4% Ag/1% ZrO2/SiO2 | 1.4 | 49.7 | 95.2 | 0 | 5.1 | 0.0 | 54.2 | 0.2 | 4.0 | 4.1 | 1.9 | 4.1 | 8.0 | 5.1 | 13.3 | 59.5 |
| 4% Ag/2% ZrO2/SiO2 | 1.4 | 61.5 | 95.8 | 7.8 | 4.5 | 0.0 | 56.6 | 1.2 | 6.5 | 2.8 | 0.6 | 2.8 | 3.5 | 4.7 | 5.2 | 62.4 |
| 4% Ag/4% ZrO2/SiO2 | 1.4 | 67.5 | 112 | 19.5 | 13.1 | 1.5 | 24.3 | 0.3 | 6.8 | 15.5 | 1.0 | 15.5 | 0.2 | 12.2 | 1.9 | 39.2 |
| 1Ag/4% ZrO2/SiO2 | 0.5 | 57.7 | 107 | 39.8 | 5.9 | 2.2 | 28.5 | 0.2 | 8.7 | 0 | 0.4 | 0 | 0.7 | 7.2 | 3.4 | 36.8 |
| 1Ag/4% ZrO2/SiO2 | 1.4 | 33.8 | 107 | 46.6 | 5.2 | 1.5 | 15.2 | 0.4 | 8.5 | 0 | 0.4 | 0 | 1.3 | 12.2 | 3.6 | 22.3 |
| 2Ag/4% ZrO2/SiO2 | 1.4 | 52.6 | 105 | 27.2 | 3.5 | 1.5 | 38.1 | 0.9 | 7.1 | 2.8 | 0.5 | 2.8 | 2.4 | 6.0 | 3.5 | 44.0 |
| 4% Ag/4% ZrO2/SiO2 | 1.4 | 67.5 | 112 | 19.5 | 13.1 | 1.5 | 24.3 | 0.3 | 6.8 | 15.5 | 1.0 | 15.5 | 0.2 | 12.2 | 1.9 | 39.2 |
| 8% Ag/4% ZrO2/SiO2 | 1.4 | 65.2 | 100.6 | 9.4 | 5.6 | 1.7 | 59.8 | 1.1 | 7.0 | 3.1 | 0.7 | 3.1 | 1.5 | 3.8 | 2.0 | 68.2 |
| 0.4Ir4Ag/ 4ZrO2/SBA16 | 0.23 | 89.1 | 80.8 | 0 | 0.1 | 1.2 | 8.7 | 2.9 | 5.1 | 1.5 | 55.3 | 0 | 0.9 | | 24.3 | 12.9 |
| 4Ag4ZrO2/ SBA16 | 0.23 | 87.1 | 103 | 3.8 | 16.7 | 2.7 | 40.7 | 0.6 | 8.6 | 1.4 | 1.6 | 1.9 | 0.1 | | 10.9 | 71.7 |
| 16Ag4ZrO2/ SiO2 | 1.4 | 66.3 | 91 | 0 | 8.8 | 1.7 | 57.8 | 1.2 | 6.0 | 3.9 | 3.1 | 3.3 | 3.4 | 3.8 | 7.0 | 69.5 |

B- Butadiene,
D- Diethylether,
A-acetylaldehyde,
C2-C5 Alkanes,
BA, Butyrlaldehyde,
BL- butanol,
Others: CO2, MeOh, PrOh, PenOH, EA, Acetic Acid, pentanone, phenol/cresol for MO277

Some examples, the conversion of ethanol to butadiene and butenes-rich olefins over Ag/ZrO$_2$/SiO$_2$ catalysts, resulted in ethanol dehydration to ethylene and Di-Ethyl-Ether (DEE) as a secondary reaction. In our study ethylene is a fuel precursor that is more desired than DEE suggesting that it might be beneficial to operate at higher temperature.

selectivity varies greatly with the Ag loading as reported in FIG. 5(*b*). The butadiene selectivity decreases drastically from ~27 to 0% with the increase of Ag loading from 1 to 8 wt. %. As the Ag loading increases, the Ag particle size increases favoring ethanol conversion to ethylene and restraining ethanol conversion to acetaldehyde intermediate to butadiene. The catalyst with 8 wt. % Ag appears promising for butenes-rich olefins production since it presents the highest olefins selectivity of ~66% with no detectable butadiene formation.

Table 7 shows that results from various examples of catalysts and process conditions. This data indicates that olefins can be made directly from ethanol with $WO_3$ or $Nb_2O_5$ replacing $ZrO_2$ and also with $Al_2O_3$ replacing $SiO_2$. What is important is to have a catalyst with mild hydrogenation activity and acid sites functionality $ZrO_2$/SBA-16 in comparison with the baseline catalyst namely 4 wt. % Ag/4 wt. % $ZrO_2$/SBA-16. The evolution of the conversion for both catalysts is similar with time on stream. FIG. 6(b) shows that the selectivity to butenes is lower for the catalyst promoted with Au. Selectivity to ethylene, butenes, butadiene, DEE and total olefins are presented in Table 4 and 5 for both 4 wt. % Ag/4 wt. % $ZrO_2$/SBA-16 and 0.5 wt. % Au_4 wt. % Ag/4 wt. % $ZrO_2$/SBA-16. The total olefins selectivity is the highest for

TABLE 7

Effect of $WO_3$ loading on the catalytic performance of 4 wt % Ag/x $WO_3$ wt %/ $Al_2O_3$. T = 325° C., P = 7 bar, WHSV = 0.23 hr$^{-1}$, 24% ethanol in $H_2$.

| Catalyst | Conversion (%) | Selectivity (%) | | | | | | | |
|---|---|---|---|---|---|---|---|---|---|
| | | Ethylene | propylene | Butenes | Liquid $C_4$-$C_8$ olefins | butadiene | C2-C5 alkanes | Oxygenates* | Cyclics hydrocarbons |
| 4 wt. % Ag/0.5 wt. % $WO_3$/$Al_2O_3$ | 99.8 | 73.3 | 0.0 | 23.6 | 0.0 | 0.0 | 0.7 | 2.4 | 0.0 |
| 4 wt. % Ag/1 wt. % $WO_3$/$Al_2O_3$ | 99.4 | 68.1 | 0.8 | 25.6 | 0.0 | 1.5 | 0.7 | 3.3 | 0.0 |
| 4 wt. % Ag/4 wt. % $WO_3$/$Al_2O_3$ | 99.9 | 77.4 | 0.0 | 18.9 | 0.0 | 0.9 | 0.7 | 2.1 | 0.0 |
| 4 wt. % Ag/8 wt. % $WO_3$/$Al_2O_3$ | 98.8 | 72.7 | 0.3 | 8.9 | 0.5 | 0.3 | 0.6 | 13.0 | 3.7 |

*Oxygenates: acetaldehyde, acetic acid, Di-ethyl-ether, CO2, acetones, 2-butanone, $C_3$-$C_4$ alcohols.

TABLE 8

Effect of the nature of the mixed oxide on the catalytic performance of 4 wt % Ag/4 wt % $MO_x$ wt %/$Al_2O_3$. T = 325° C., P = 7 bar, WHSV = 0.23 hr$^{-1}$, 24% ethanol in $H_2$.

| Catalyst | Conversion (%) | Selectivity (%) | | | | | | | | |
|---|---|---|---|---|---|---|---|---|---|---|
| | | Ethylene | Propylene | butenes | Hexnes | Liquid $C_4$-$C_8$ olefins | butadiene | C2-C5 alkanes | Oxygenates* | Cyclics hydrocarbons |
| 4 wt. % Ag/4 wt. % $WO_3$/$Al_2O_3$ | 99.9 | 77.4 | 0.0 | 18.9 | 0.0 | 0.0 | 0.9 | 0.7 | 2.1 | 0.0 |
| 4 wt. % Ag/4 wt. % $Nb_2O_5$/$Al_2O_3$ | 99.8 | 49.2 | 1.2 | 35.6 | 4.5 | 0.0 | 4.3 | 0.5 | 4.7 | 0.0 |

The catalytic performance of the 4 wt. % Ag/4 wt. % $ZrO_2$/SBA-16 catalyst was first compared with the one for a catalyst promoted with Au (i.e. 0.5 wt. % Au_4 wt. % Ag/4 wt. % $ZrO_2$/SBA-16) while operating at 325° C. As can be seen from Table 9, while operating under the same conditions, the catalysts promoted with Au present higher conversion of 94.4% and a higher total olefins selectivity of 85.4%. We have thus conducted additional experiments at a higher temperature equal to 400° C.

FIG. 6 (a) presents the evolution of the conversion with time on stream for the 0.5 wt. % Au_4 wt. % Ag/4 wt. %

0.5 wt. % Au_4 wt. % Ag/4 wt. % $ZrO_2$/SBA-16 and equal to 57.3% but it mainly due to the contribution of less desired ethylene for which the selectivity is equal to 52.6%. Although low, the butenes selectivity after about 100 hours on stream is higher for 4 wt. % Ag/4 wt. % $ZrO_2$/SBA-16 than for 0.5 wt. % Au_4 wt. % Ag/4 wt. % $ZrO_2$/SBA-16. Hence, while operating at 400° C., adding Au promoter to the 4 wt. % Ag/4 wt. % $ZrO_2$/SBA-16 baseline catalyst does not seem beneficial since both stability and butenes selectivity are not improved.

TABLE 9

Catalytic performance of 4 wt. % Ag/4 wt. % ZrO$_2$/SBA-16 catalyst and 0.5 wt. % Au _4wt. % Ag/4 wt. % ZrO$_2$/SBA-16 at T = 325° C., P = 7 bar, WHSV = 0.23 hr$^{-1}$, 24% ethanol in H$_2$.

| Catalyst | Conversion (%) | Selectivity (%) | | | | | |
|---|---|---|---|---|---|---|---|
| | | ethylene | butenes | butadiene | DEE | Total olefins | Acetaldehyde |
| Without Au 4 wt. % Ag/4 wt. % ZrO$_2$/SBA-16 | 83.8 | 6.9 | 60.6 | 0.9 | 12.5 | 74.8 | 4.1 |
| With Au 0.5 wt. % Au _4 wt. % Ag/4 wt. % ZrO$_2$/SBA-16 | 94.4 | 12.2 | 69.0 | 0.0 | 7.1 | 85.4 | 0.6 |

TABLE 10

Catalytic performance of 4 wt. % Ag/4 wt. % ZrO$_2$/SBA-16 catalyst with time on stream (TOS) at T = 400° C., P = 7 bar, WHSV = 1.82 hr$^{-1}$, 24% ethanol in H$_2$.

| TOS (hours) | Conversion (%) | Selectivity (%) | | | | |
|---|---|---|---|---|---|---|
| | | ethylene | Butenes | butadiene | DEE | Total olefins |
| 1.5 | 97.6 | 15.3 | 70.1 | 0.0 | 3.5 | 89.0 |
| 5.0 | 96.6 | 15.5 | 57.2 | 11.8 | 4.8 | 76.7 |
| 19.4 | 88.1 | 17.6 | 16.2 | 45.0 | 7.9 | 37.2 |
| 45.5 | 70.7 | 21.3 | 11.1 | 41.4 | 11.1 | 35.2 |
| 74.9 | 61.4 | 24.1 | 9.5 | 37.9 | 13.5 | 36.1 |
| 101 | 55.4 | 27.5 | 7.6 | 33.0 | 16.0 | 37.3 |

TABLE 11

Catalytic performance of 0.5 wt. % Au_4 wt. % Ag/4wt. % ZrO$_2$/SBA-16 catalyst with time on stream (TOS) at T = 400° C., P = 7 bar, WHSV = 1.82 hr$^{-1}$, 24% ethanol in H$_2$.

| TOS (hours) | Conversion (%) | Selectivity (%) | | | | |
|---|---|---|---|---|---|---|
| | | ethylene | butenes | butadiene | DEE | Total olefins |
| 4.9 | 94.1 | 21.0 | 23.7 | 37.9 | 7.1 | 49.1 |
| 23.6 | 74.0 | 34.8 | 11.0 | 30.9 | 14.5 | 48.2 |
| 41.5 | 64.0 | 44.1 | 7.3 | 23.0 | 17.3 | 53.3 |
| 67.5 | 58.9 | 48.8 | 4.9 | 16.1 | 21.7 | 55.0 |
| 96.5 | 52.9 | 52.6 | 3.6 | 11.9 | 23.3 | 57.3 |

The catalytic performance and stability of the 4 wt. % Ag/4 wt. % ZrO$_2$/SBA-16 catalyst was compared with the one for a catalyst promoted with Re (i.e. 0.5 wt. % Re_4 wt. % Ag/4 wt. % ZrO$_2$/SBA-16) while operating at 400° C. As can be seen from FIG. 6 (a), the catalyst promoted with Re is more stable since the conversion decreases only from 99.4% (TOS=4.9 hours) to 73.0% (TOS=102.2 hours) while for the baseline 4 wt. % Ag/4 wt. % ZrO$_2$/SBA-16 catalyst the conversion decreases from 96.6% (TOS=5.0 hours) to 55.4% (TOS=101 hours). Similarly, the selectivity to butenes decreases more slowly with the Re promoted catalyst and is equal to 26.5% at TOS=102.2 hours as opposed to 7.6% at TOS=101 hours for the 4 wt. % Ag/4 wt. % ZrO$_2$/SBA-16 catalyst. Hence, the Re promoter has a beneficial effect on both the conversion and the butenes selectivity. Selectivity to ethylene, butenes, butadiene, DEE and total olefins are presented in Table 12 for 0.5 wt. % Re_4 wt. % Ag/4 wt. % ZrO$_2$/SBA-16. One can see that the total olefins selectivity is equal to 48.9% after 102.2 hours with only 14.6% selectivity to ethylene.

TABLE 12

Catalytic performance of 0.5 wt. % Re _4wt. % Ag/4 wt. % ZrO$_2$/SBA-16 catalyst with time on stream (TOS) at T = 400° C., P = 7 bar, WHSV = 1.82 hr$^{-1}$, 24% ethanol in H$_2$.

| TOS (hours) | Conversion (%) | Selectivity (%) | | | | |
|---|---|---|---|---|---|---|
| | | ethylene | butenes | butadiene | DEE | Total olefins |
| 4.9 | 99.4 | 0.8 | 26.8 | 0.0 | 2.0 | 28.6 |
| 21.4 | 95.7 | 8.5 | 60.4 | 4.5 | 4.7 | 60.4 |
| 44.9 | 90.7 | 13.0 | 34.5 | 21.0 | 6.3 | 51.1 |
| 68.9 | 80.6 | 14.1 | 27.2 | 25.2 | 8.0 | 44.4 |
| 102.2 | 73.0 | 14.6 | 26.5 | 25.9 | 7.5 | 48.9 |

Figures 7A, 7B:
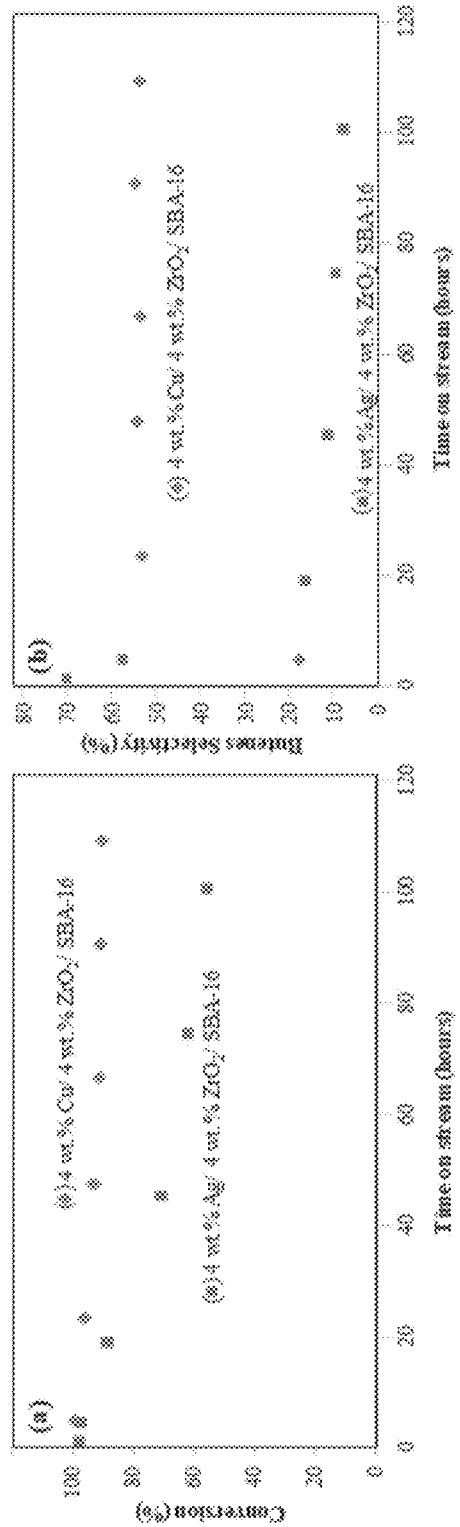
FIG. 7(a) shows the conversion with time on stream for 4 wt. % Ag/4 wt. % ZrO$_2$/SBA-16 catalyst and 4 wt. % Cu/4 wt. % ZrO$_2$/SBA-16 at T=400° C., P=7 bar, WHSV=1.82 hr$^{-1}$, 24% ethanol in H$_2$.
FIG. 7(b) shows the butenes selectivity with time on stream for 4 wt. % Ag/4 wt. % ZrO$_2$/SBA-16 catalyst and 4 wt. % Cu/4 wt. % ZrO$_2$/SBA-16 at T=400° C., P=7 bar, WHSV=1.82 hr$^{-1}$, 24% ethanol in H$_2$.

The catalytic performance and stability of the baseline 4 wt. % Ag/4 wt. % ZrO$_2$/SBA-16 catalyst was compared with the one for a catalyst where Ag was replaced with Copper (Cu) labeled as 4 wt. % Cu/4 wt. % ZrO$_2$/SBA-16. For both catalysts the conversion with time on stream is displayed in FIG. 7(a). While the conversion decreases from 96.6% (TOS=5.0 hours) to 55.4% (TOS=101 hours) for 4 wt. % Ag/4 wt. % ZrO$_2$/SBA-16 the conversion decreases only from 99.1% (TOS=5.0 hours) to 90% (TOS=109.4 hours) for 4 wt. % Cu/4 wt. % ZrO$_2$/SBA-16. Hence, the results clearly show that the supported Cu catalyst deactivates less quickly than the supported Ag catalyst. Additionally, for 4 wt. % Cu/4 wt. % ZrO$_2$/SBA-16 the butenes selectivity increases from 17.7% after 5.0 hours on stream to 53.2% after 23.5 hours on stream and then remains stable for the duration of the test, as depicted in FIG. 7(b).

On the contrary, the butenes selectivity keeps decreasing with time on stream and attains less than 7.6% after 101 hours on stream for 4 wt. % Ag/4 wt. % ZrO$_2$/SBA-16. Selectivity to ethylene, butenes, butadiene, DEE and total olefins are presented in Table 13 for 4 wt. % Cu/4 wt. % ZrO$_2$/SBA-16. One can see that after an initial induction period of about 23.5 hours the selectivity to the products is quite stable and no butadiene is formed. The 4 wt. % Cu/4 wt. % ZrO$_2$/SBA-16 catalysts is thus a promising candidate for the direct conversion of ethanol to butenes since stable yield of butenes rich olefins was observed for 100+ hours on stream and at commercially relevant throughput (i.e. WHSV=1.82 hr$^{-1}$).

TABLE 13

Catalytic performance of 4 wt. % Cu/4wt. % ZrO$_2$/SBA-16 catalyst with time on stream (TOS) at T = 400° C., P = 7 bar, WHSV = 1.82 hr$^{-1}$, 24% ethanol in H$_2$.

| TOS (hours) | Conversion (%) | Selectivity (%) | | | | |
|---|---|---|---|---|---|---|
| | | ethylene | butenes | butadiene | DEE | Total olefins |
| 5.0 | 99.1 | 0.6 | 17.7 | 3.9 | 2.9 | 19.9 |
| 23.5 | 96.0 | 11.1 | 53.2 | 0 | 3.7 | 78.3 |
| 47.8 | 92.9 | 12.0 | 54.0 | 0 | 4.1 | 80.3 |
| 66.8 | 91.1 | 12.1 | 53.4 | 0 | 4.2 | 78.9 |
| 90.9 | 91.0 | 11.8 | 54.7 | 0 | 4.3 | 79.0 |
| 109.4 | 90.0 | 12.2 | 53.7 | 0 | 4.6 | 76.8 |
| 129.1 | 89.6 | 11.6 | 51.2 | 0 | 4.4 | 76.5 |

As the aforementioned data demonstrates better performance is obtained when both transition metal sites and acid sites are present. Higher % of transition metal dispersion helps addresses conversion but does not always affect the selectivity of the reaction to butenes. Butenes are produced from butadiene partial hydrogenation in the presence of H2 carrier and butadiene is produced from acetaldehyde over the acid sites. Hence, the right balance of transition metal sites and acid sites appears to be related to the specified performance.

The data disclosed demonstrates that the ethanol conversion increases with the transition metal dispersion for transition metal oxides on silica supports. Metal dispersion as well as a Lewis acid site concentration between 10 and 35 µmoles/grams (see Appl. Catal. B, 2018, v236, p 576-587) in some cases in addition to operating in the presence of H2 carrier and while operating at elevated pressure 7 bar allows for direct conversion of ethanol to butenes with selectivity greater than 13%. SBA-16 with its particular mesoporous structure (cubic with bimodal pore sizes) has shown the best results so far, even when the ethanol containing feedstock contains water. The recited structures and process take advantage of the relatively weak hydrogenation ability of the transition metal such as Ag and mildly acidic support materials provide a preference for carbon to oxygen and carbon to carbon coupling take place without hydrogen saturation.

While various preferred embodiments of the disclosure are shown and described, it is to be distinctly understood that this disclosure is not limited thereto but may be variously embodied to practice within the scope of the following claims. From the foregoing description, it will be apparent that various changes may be made without departing from the spirit and scope of the disclosure as defined by the following claims.

What is claimed is:

1. A process for producing butenes from a feed stream containing ethanol in a single step, the process comprising the steps of:

passing a feed stream containing ethanol in a gas phase over a catalyst of 0.5 wt. % Au_4 wt. % Ag/4 wt. % ZrO$_2$/SBA-16 catalyst having a transition metal oxide with a transition metal dispersion of at least 30% by volume on a silica support, wherein the transition metal is Ag, Cu, or Re, in the presence of a hydrogen containing carrier gas, at a preselected temperature and a preselected pressure to directly form butenes from the ethanol with selectivity equal or greater than 13%, thereby producing a product stream comprising butenes; and recovering the formed butenes from the product stream.

2. A process for producing butenes from a feed stream containing ethanol in a single step, the process comprising the steps of:

passing a feed stream containing ethanol in a gas phase over a catalyst having a transition metal oxide with a transition metal dispersion of at least 30% by volume on a silica support, wherein the transition metal is Ag, Cu, or Re, in the presence of a hydrogen containing carrier gas, at a preselected temperature and a preselected pressure to directly form butenes from the ethanol with selectivity equal or greater than 13%, wherein the catalyst is a 0.5 wt. % Re_4 wt. % Ag/4 wt. % ZrO$_2$/SBA-16 catalyst, thereby producing a product stream comprising butenes; and recovering the formed butenes from the product stream.

3. A process for producing butenes from a feed stream containing ethanol in a single step, the process comprising the steps of:

passing a feed stream containing ethanol in a gas phase over a catalyst having a transition metal oxide with a transition metal dispersion of at least 30% by volume on a silica support, wherein the transition metal is Ag, Cu, or Re, in the presence of a hydrogen containing carrier gas, at a preselected temperature and a pressure of 70 atm to directly form butenes from the ethanol with selectivity equal or greater than 13%, thereby producing a product stream comprising butenes, thereby producing a product stream comprising butenes; and recovering the formed butenes from the product stream.

* * * * *